(12) United States Patent
Hardt et al.

(10) Patent No.: US 11,504,258 B2
(45) Date of Patent: *Nov. 22, 2022

(54) DEVICE FOR SUPPORTING AT LEAST ONE ARM OF A USER

(71) Applicant: Ottobock SE & Co. KGaA, Duderstadt (DE)

(72) Inventors: Alexander Hardt, Asslar (DE); Olaf Kroll-Orywahl, Northeim (DE)

(73) Assignee: Ottobock SE & Co. KGaA, Duderstadt (DE)

( * ) Notice: Subject to any disclaimer, the term of this patent is extended or adjusted under 35 U.S.C. 154(b) by 234 days.

This patent is subject to a terminal disclaimer.

(21) Appl. No.: 16/538,030

(22) Filed: Aug. 12, 2019

(65) Prior Publication Data

US 2020/0078200 A1 Mar. 12, 2020

(30) Foreign Application Priority Data

Aug. 14, 2018 (DE) ...................... 10 2018 119 755.1

(51) Int. Cl.
*A61F 5/01* (2006.01)
(52) U.S. Cl.
CPC ...... *A61F 5/013* (2013.01); *A61F 2005/0137* (2013.01); *A61F 2005/0146* (2013.01); *A61F 2005/0155* (2013.01); *A61F 2005/0167* (2013.01)
(58) Field of Classification Search
CPC .......... A61F 5/013; A61F 5/03; A61F 5/0118; A61F 5/3761; A61F 5/37; A61F 5/3753; A61F 5/00; A61F 2005/0137; A61F 2005/0146; A61F 2005/0155; A61F 2005/0167; A61F 2005/0174; A61F 5/01; B25J 9/0006; B25J 9/00; A63B 21/028; A63B 23/16; A61H 2201/0165; A61H 2201/5064; A61H 2201/1607; A61H 2201/1207; A61H 2201/5084;

(Continued)

(56) References Cited

U.S. PATENT DOCUMENTS 5,685,830 A * 11/1997 Bonutti ................. A61F 5/0123
601/33
9,427,865 B2 * 8/2016 Doyle .................. B25J 19/0008
(Continued)

FOREIGN PATENT DOCUMENTS

| DE | 102004008124 A1 | 9/2005 |
|---|---|---|
| DE | 102017112436 A1 | 12/2018 |
| EP | 3156193 A1 | 4/2017 |

(Continued)

*Primary Examiner* — Alireza Nia
*Assistant Examiner* — Daniel A Miller
(74) *Attorney, Agent, or Firm* — WCF IP

(57) ABSTRACT

A device for supporting at least one arm of a user includes one or more arm support elements each of which has an arm shell for placing the at least one arm of the user on the arm shell. Force is applied to the arm support elements by at least one passive actuator. A counter bearing for the applied force includes a force transmission element and a counter bearing element. A force application lever is engaged by the one passive actuator and is connected to the arm support or the force transmission element. The force application lever is torque proof and confines an angle which is adjustable.

7 Claims, 5 Drawing Sheets

(58) Field of Classification Search
CPC ...... A61H 2201/165; A61H 2201/1638; A61H 2201/5069; A61H 1/02; A61H 1/0274
USPC .......................................................... 602/16
See application file for complete search history.

(56) References Cited

U.S. PATENT DOCUMENTS

2016/0081871 A1    3/2016  Doyle
2016/0339583 A1*  11/2016  Van Engelhoven ..... B25H 1/10

FOREIGN PATENT DOCUMENTS

| JP | H04 304979 A | 10/1992 |
| WO | 2014/093408 A2 | 6/2014 |
| WO | 2014/195373 A1 | 12/2014 |

* cited by examiner

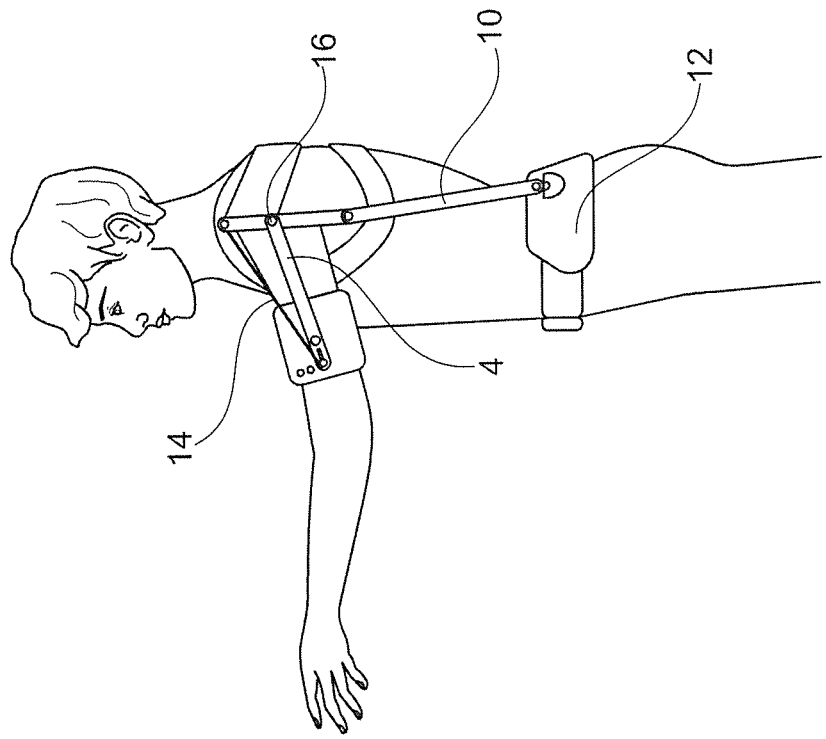
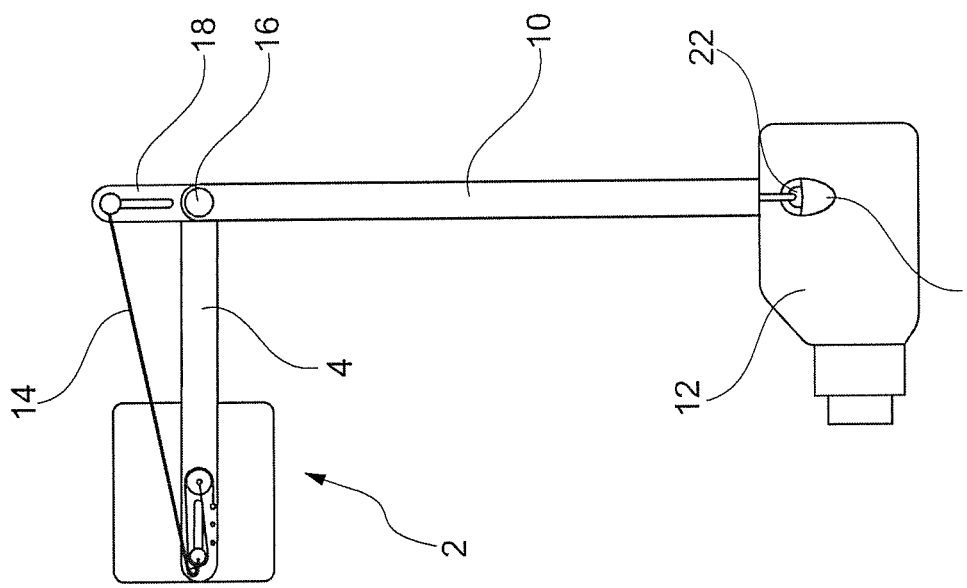
Fig. 4
Fig. 3

DEVICE FOR SUPPORTING AT LEAST ONE ARM OF A USER

FIELD OF THE INVENTION

The invention relates to a device for supporting at least one arm of a user, wherein the device has at least one arm support element, each of which has an arm shell for placing on an arm, at least one passive actuator, which is configured to apply a force to at least one of the arm support elements, and at least one counter bearing for the force to be applied, which comprises at least one force transmission element and a counter bearing element, wherein the device features at least one force application lever, which is connected to one of the arm support elements or the force transmission element such that it is torque-proof and confines an angle, and with which the at least one passive actuator engages.

BACKGROUND

This type of device is described, for instance, in DE 10 2017 112 436, which has not been pre-published.

Devices that can be used to support arms are known from various documents. The device described in US 2016/0081871 A1 features, for example, a counter bearing element that is designed in the form of a strap that can be placed around torso of the user. Two support braces run along the user's back to his shoulder, each of said support braces being connected to a joint above and laterally next to the shoulder of the user, such that the arm can be raised. These are the force transmission elements. Spring elements are arranged on the corresponding joints, by means of which an upward force can be exerted on the arm shells, such that the arms can be supported, for example when lifting heavy objects or when working above one's head. If the arms are lowered, a pressure must be exerted by the arms onto the arm shells, wherein this pressure exceeds the force applied by the spring elements, thereby causing the arms to lower.

WO 2014/0093804 A1 and U.S. Pat. No. 9,427,865 B2 describe a similar device, each of which features a spring, especially a tension spring, that is connected to a Bowden cable, said spring functioning as a mechanical energy storage device which acts a passive actuator. The Bowden cable is guided by way of a pulley in such a way that, upon a swiveling of an arm, meaning a movement of the arm support element relative to the counter bearing element, the spring is stretched, such that the mechanical energy storage device is charged with energy.

EP 3 156 193 A1 describes an active device which supports arms during work carried out above the head. The arm shells are connected to one another by a number of different joints and connecting frame elements. This should render as many movements as possible which are executable by a shoulder joint also possible with the mounted device. However, due to the number of elements, this device is large, structurally intricate and therefore expensive. Further support devices, especially devices which support the lifting of heavy objects or work performed above a user's head, are known from WO 2014/195373 A1 and US 2016/339583 A1.

The disadvantage of all the named devices is that the force that can be applied to the arm support element by the at least one passive actuator is dependent, where applicable, on the angle between the arm support element and the force transmission element, and that the size of the force can indeed be adjusted, but the force path is determined by the structure of the respective device.

This is a disadvantage, for example, if the device is to be used successively by two users of a different size. While a shorter user must raise their arms fully above their head in order to work in a particular workpiece, a taller user need only partially raise their arms. The structure known from the prior art also poses a disadvantage when an individual user is to execute different activities at different heights or the users of the device have different degrees of strength, meaning that they require different degrees of support. The invention thus aims to remedy these disadvantages or at least to reduce them.

SUMMARY

The invention solves the task at hand by way of a device for supporting at least one arm of a user according to the generic term in claim 1, which is characterized by the fact that the angle between the force application lever and the arm support element or the force application level and the force transmission element is adjustable.

The at least one passive actuator can be used to exert a force on the arm support element, wherein this force acts on a force application lever. In a first configuration, the force application lever is connected to one of the arm support elements such that it is torque-proof, wherein the force that can be exerted by the actuator is to be applied to said arm support element. In this case, the actuator may be a spring or an elastic element, for instance, the end of which is arranged, for example, on the counter bearing. The other end engages with the force application lever. The arm support element is preferably arranged on the force transmission element such that it can be swiveled. As the force application lever in this first configuration is arranged on the arm element such that it is torque-proof, the force transmission lever is consequently also fixed to the force transmission element such that it is pivotable. As a result of the force from the passive actuator that is acting on the force transmission lever, a torque—and thus a supporting force—is exerted on the arm support element. This torque is at its greatest when the force transmission lever is standing perpendicular to the direction of the acting force.

If a user of such a device raises their arm, the arm support element and thus also the force application lever that is connected to it such that it is torque-proof, is swiveled about the force transmission element. The angle between the force application lever and the force transmission element changes as a result. At the same time, the angle between the force application lever and the effective direction of the force that can be exerted by the at least one passive actuator changes. When the arms are in a particular position, the force application lever stands perpendicular to the direction of the acting force. At this point, the torque applied by the actuator to the force application lever and thus also to the arm support element is at its greatest; the supporting force for the arm and the arm support element is therefore also at its maximum.

According to the invention, the angle between the arm support element and the force application lever should now be adjustable. Consequently the angle can be changed and can be set in at least two, preferably many, especially preferably an infinite number of positions, such that a torque-proof connection between the force application lever and the arm support element is achieved. By adjusting the angle, the position of the arms of the user can be changed, wherein the force application lever in this position stands perpendicular to the force that can be exerted by the at least one actuator.

In another configuration the force application lever is fixed to the force transmission element such that it is torque-proof. In this case, the actuator may also be a spring or an elastic element, for instance, the end of which is now no longer arranged on the force transmission element or the counter bearing, but rather is connected to the arm support element. The other end of the actuator is connected to the force application lever. In this case, a torque can also be exerted on the force application lever by the at least one passive actuator, such that a supporting force is exerted on the arm support element. In this case, it is also beneficial if the arm support element is arranged on the force transmission element such that it can be rotated.

In this configuration, the torque generated by the at least one passive actuator, and therefore the force that can be applied to the arm support element, is also at its maximum when the angle between the force application lever and the acting force exerted by the actuator is 90°. If the angle between the force application lever and the force transmission element is now adjustable, it is also possible in this configuration to change the position in which the torque, and therefore the supporting force, is at its maximum.

With regards to the present invention, if reference is made to a direction of the force application lever or an angle between a structural component and the force application lever, this direction always refers to the direction from the point of force application, i.e. the point at which the force that can be exerted by the actuator acts on the force application lever, and the pivot point about which the arm support element can be swiveled relative to the force transmission element.

In a preferred configuration of the present invention, the force application lever can be brought into a first state, in which it can be swiveled relative to the arm support element and the force transmission element, and a second state, in which it is arranged with the arm support element or the force transmission element such that it is torque-proof. While the force application lever is in the first position, an angle between the force application lever and the arm support or the force application lever and the force transmission element is adjustable. It can be changed by swiveling the force application lever. Once the desired angle has been set, the force application lever is moved into the second position, so that it can no longer be rotated relative to the arm support element and the force transmission element.

The device preferably features two arm support elements, each of which has an arm shell for placing on an arm of the user.

In a preferred configuration, the force transmission element and/or the arm support element has two structural components that are connected to one another by a swivel joint, thereby rendering an angle between these two structural components adjustable. The swivel joint can preferably be loosened and tightened. As a result of this configuration of the swivel joint, a direction of the force transmission element can be changed. The direction of the force transmission element, which may be important, for example, in determining the angle between the force transmission element and the force application element, is the direction between the pivot point about which the arm support element can be swiveled relative to the force transmission element, and the bearing point at which the force transmission element is arranged on the counter bearing element.

In a preferred embodiment, the counter bearing element of the counter bearing refers, for example, to a hip strap that worn by the user of the device around the hips or the stomach. The force transmission element is, for instance, a rod that comprises one or several structural components, wherein one or several swivel joints may be arranged between several structural components of the rod; the angle between the individual structural components can be adjusted or set by way of said swivel joint(s). This force transmission element is fixed at one end to the counter bearing element. At the other end, the arm support element is arranged such that it can be swiveled about a swivel joint, said arm support element being designed, for example, as a spacer element in the form of a rod, which may be telescopic or non-telescopic. All directions that are used to determine the angle, which should be adjustable according to the invention, are directed towards the respective pivot point of this swivel joint. If the force application lever is connected to the arm support element such that it is torque-proof, the angle is formed between the direction between the force application point on the force application lever and the pivot point of the swivel joint on the one hand and the direction of the force transmission element on the other, wherein the latter direction is formed by the connecting line between the pivot point of the swivel axis on the one hand and the bearing point on the other, at which the force transmission element is positioned on the counter bearing.

If however the force application lever is connected to the force transmission element such that it is torque-proof, the angle is determined between the direction of the force application lever, i.e. the direction between the force application point and the pivot point of the swivel joint, on the one hand and the direction of the arm support element, i.e. the direction between the arm shell in which the arm is placed, and the pivot point of the swivel joint between arm support element and force transmission element on the other.

The force transmission element preferably features at least a first structural component and a second structural component, which are connected to one another by a joint. It is especially advantageous if the first structural component and/or the second structural component is/are rods or bars, which are connected to one another via a hinge or a swivel joint, which comprises a single swivel axis. Preferably, a compressive force can be transmitted by way of the force transmission element, which forms part of the counter bearing. The arm support element should be supported by a force that acts from below. The force transmission element should transmit the corresponding counter force into the counter bearing, so it must be able to transmit compressive forces. If this is ensured, the flexible arrangement of the two structural components of the force transmission element to one another means that an optimal configuration of the force transmission element is achieved, depending on the movement and/or position of the user. The two structural components of the force transmission element can re-align themselves relative to one another by one of the structural components swiveling about the swivel axis relative to the other structural component. This enables distances between the counter bearing element and the support element to be changed and adapted to fit the respective position and/or movement of the user.

It is especially preferable if the first structural component and/or the second structural component are designed to be adjustable in length. Each length-adjustable structural component can be designed as a telescopic rod. This renders it especially easy to adapt the device to different-sized users, as the telescopic properties or ability to adjust the length of at least one of the structural components means that the entire length of the force transmission element can also be adjusted. It is especially preferable if the length of the length-adjustable first structural component and/or the length-adjustable second component can be changed in different positions, preferably infinitely, but also locked in different positions, such that the one-time desired length can be set and no longer changed without releasing a corresponding fixing mechanism.

The joint preferably refers to a swivel joint with a swivel axis.

In an especially preferred configuration, the first structural component and/or the second structural component are connected to the joint such that a movement of the respective structural component about its longitudinal axis relative to the joint is possible. It is preferable if the arm support element is located at the upper end of one of the two structural components that faces away from the counter bearing element. The arm support element and especially a spacer element of the arm support element is preferably arranged on the respective structural component of the force transmission element such that it can be swiveled. If this structural component, on which the arm support element is situated, be configured relative to the joint between the first structural component and the second structural component such that it can be rotated about its longitudinal axis, the arm support element may also be designed such that it can be rotated about the longitudinal axis of the respective structural component. This renders further movements possible, so that the position of the arm support element and especially the extension and, where applicable, the shape of the respective force transmission element can be adapted to the position and/or movement of the user of the device.

The force transmission element is preferably arranged on the counter bearing element such that it can be rotated and/or swiveled. To this end, the force transmission element can be fixed to the counter bearing element by way of a hinge, a ball joint or another joint for instance, or for example plugged or inserted at one end of the force transmission element into a pocket or bracket on the counter bearing element specifically provided for that purpose. In an especially preferred configuration, one of the structural components of the force transmission element is consequently arranged on the counter bearing element such that it can be rotated and/or swiveled, and the respective structural component arranged such that it can be rotated about its own longitudinal axis relative to the joint, the respective structural component being connected to the respective other structural component of the force transmission element by way of said joint. It is particularly preferable if this other structural component is also fixed to the joint between the two structural components such that it can be rotated about its longitudinal axis. This renders possible an extensive movement of the structural components of the force transmission element relative to one another, relative to the counter bearing element and preferably also relative to the arm support element. The arm support element comprises the splint in which the arm is placed. Due to the configuration of the force transmission element, which allows for it to be positioned, rotated and swiveled in various ways, this splint can be brought into a number of different positions, meaning that it not only possible to follow a movement of the actual shoulder joint, i.e. a ball joint, but also that other movements are also possible that are the result of a movement of the entire shoulder.

The counter bearing element is preferably a mounting element for placing the device on the torso of the user. It may be a strap, a belt, a bandage or a shell element and can preferably be integrated into an item of clothing, such as trousers or a jacket. Alternatively or additionally, the counter bearing element comprises a shoulder element for placing the device on a shoulder of the user.

The force transmission element preferably comprises several, preferably two-dimensional, partial elements that are designed such that they can displaced relative to one another. These partial elements are preferably bent and, in an especially preferable scenario, comprise at least partially the same radius of curvature. For example, they may be designed to be arc-shaped. They have a first direction of extension which is greater than a second direction of extension that runs perpendicular to it. The partial elements are configured along this first direction of extension such that they can be displaced relative to one another, such that a displacement of the at least two partial element allows for the adjustment of the length and a total angle of curvature of the force transmission element. If the force transmission element consists of more than two, for example three, four or five partial elements, arranged adjacently such that they can be displaced !! in pairs, a total angle of curvature of the force transmission element can be adjusted at least partially, but preferably completely, independently of the length of the force transmission element. To this end, it is beneficial if the various partial elements have the same radius of curvature in the areas in which they lie on top of one another and can be displaced relative to one another; otherwise they should have different radii of curvature.

The partial elements are preferably made of metal, such as steel, or a plastic or a fiber-reinforced plastic, in particular carbon fiber-reinforced plastic.

DESCRIPTION OF THE DRAWINGS

In the following, examples of embodiments of the present invention will be explained in more detail by way of the attached drawings: They show.

DETAILED DESCRIPTION

Figure 1:
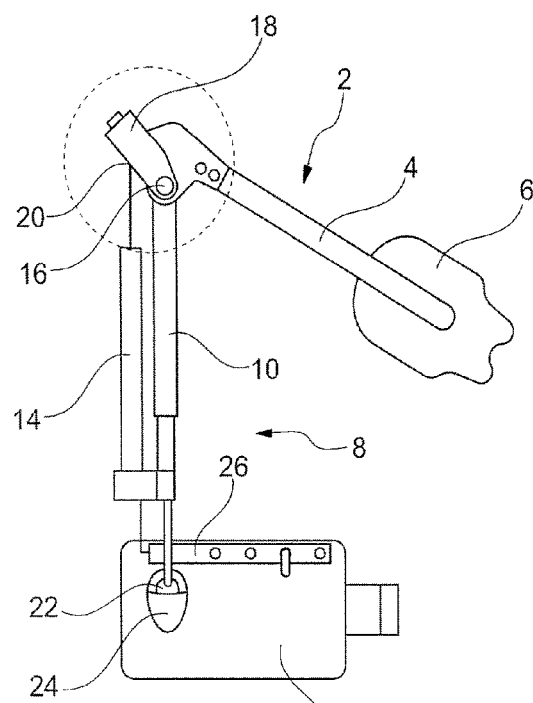
FIG. 1—the schematic depiction of a first example of an embodiment of the present invention, FIG. 2A—the schematic depiction of a further example of an embodiment of the present invention, FIG. 2B—the schematic depiction of the embodiment of FIG. 2A with two arm support elements, FIG. 3—the schematic depiction of a further example of an embodiment, FIG. 4—the schematic depiction of an example of an embodiment of the present invention when in the mounted state, FIG. 5—a further schematic depiction of an example of an embodiment, FIG. 6—the schematic depiction of a further example of an embodiment of the present invention, FIG. 7—the schematic depiction of a further example of an embodiment of the present invention, FIG. 8—an enlarged depiction of a part of FIG. 7, and FIGS. 9 and 10—the schematic depiction of a force transmission element made of three partial elements.

FIG. 1 shows a device for supporting an arm of the user that comprises an arm support element 2 with a spacer element 4 as well as an arm shell 6, and that features a counter bearing 8 which, in the example of an embodiment shown, comprises a force transmission element 10 and a counter bearing element 12. The device also has a passive actuator 14 in the form of an elastic element.

The arm support element 2 is fixed to the force transmission element 10 of the counter bearing such that it can be swiveled about a swivel axis 16, which may also be referred to as a rotational axis. A force application lever 18 is also arranged on the arm support element 2 such that it is torque-proof, wherein a force application point 20 is situated on said force application lever on which the force that can be exerted by the passive actuator 14 acts.

The force application lever 18 can be brought into two states. In the example of an embodiment shown, it is depicted in the first state, in which it is arranged on the arm support element 2 and especially on the spacer element 4 such that it is torque-proof. However, it can be brought into a second state, in which it is arranged such that it can be swiveled relative to the spacer element 4 of the arm support element 2. This renders it possible to set an angle between the force application lever 18 and the arm support element 2. Here, the angle is formed between two directions. One direction is the direction of the force application lever 18, which is the direction between the force application point 20 and the swivel axis 16. The second direction, which is required for determining the angle, is the direction of the arm support element 2. This refers to the angle between the arm shell 6, in which the arm is placed, and the swivel axis 16.

A lower end 22 of the force transmission element 10, said end forming a bearing point in the example of an embodiment shown, is positioned in a pocket 24, which is arranged on the counter bearing element 12. The lower end of the passive actuator 14 is arranged on the counter bearing element 12 via a tension element 26. This enables a force that is transmitted from the passive actuator 14 to the force application lever 18 to be transmitted via the counter bearing 8 to the body of the user. The lower end 22 can be swiveled and rotated in the pocket 24, so that an optimal position of the counter bearing 8 can be achieved for each position of the arm.

Figure 2A:
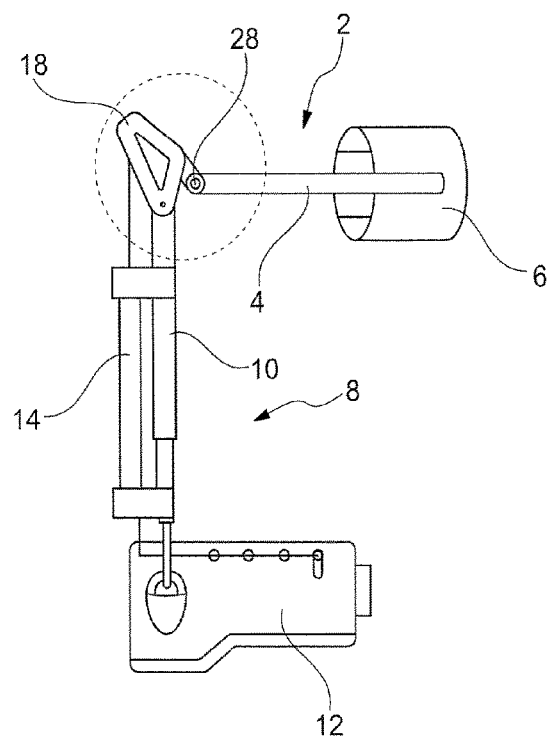
Figure 2B:
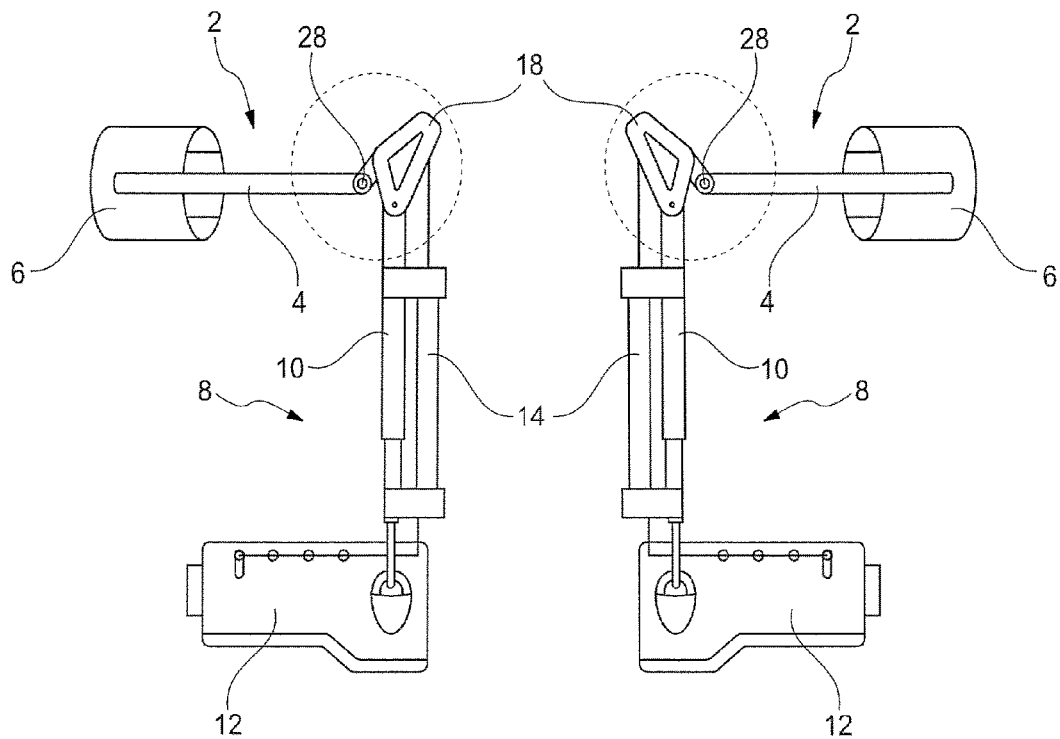

FIG. 2A shows an alternative configuration. It also features an arm support element 2 with a spacer element 4 and an arm shell 6, as well as a counter bearing 8 with a force transmission element 10 and a counter bearing element 12 as well as a passive actuator 14. Unlike the embodiment depicted in FIG. 1, a further swivel joint 28 is arranged between the spacer element 4 of the arm support element 2 and the force application lever 18, wherein said swivel joint is designed such that it can be swivelled but tightened. A change of the angle of the swivel joint allows for an angle between the force application lever 18 and the spacer element 4 to be adjusted, such that the position of the arm and therefore of the arm shell 6 is also designed to be adjustable, said position referring to the position in which the force transmitted to the force application lever 18 by the passive actuator 14, and thus also the supporting force, is at its maximum. FIG. 2B shows the configuration of FIG. 2A, but with two arm support elements, each of which has an arm shell for placing on an arm of the user.

FIG. 3 shows an alternative embodiment. Unlike the embodiments depicted in FIGS. 1 and 2, the force application lever 18 here is connected to the force transmission element 10 such that it is torque-proof. The passive actuator 14 is arranged in the form of an elastic element between the force application lever 18 and an element of the arm support element 2. The spacer element 4 of the arm support element 2 is again arranged on the force transmission element 10 such that it can be swiveled about the swivel axis 16. The end 22 of said force transmission element is again positioned in the pocket 24 of the counter bearing element 12.

In the example of an embodiment shown, the angle between the force application lever 18 and the force transmission element 10 can be adjusted and determined. This renders is possible to adjust the position of the arm in particular and therefore of the arm support element 2, said position referring to the position in which the force applied from the passive actuator 14 is at its maximum.

FIG. 4 shows a configuration of the invention when in the mounted state that is similar to the example of an embodiment in FIG. 3. The counter bearing element 12 is arranged around the hips of the wearer. The spacer element 4 of the arm support element 2 is arranged on the force transmission element 10 such that it can be swiveled about the swivel axis 16. The passive actuator 14 is designed in the same way as in FIG. 3.

Figure 5:
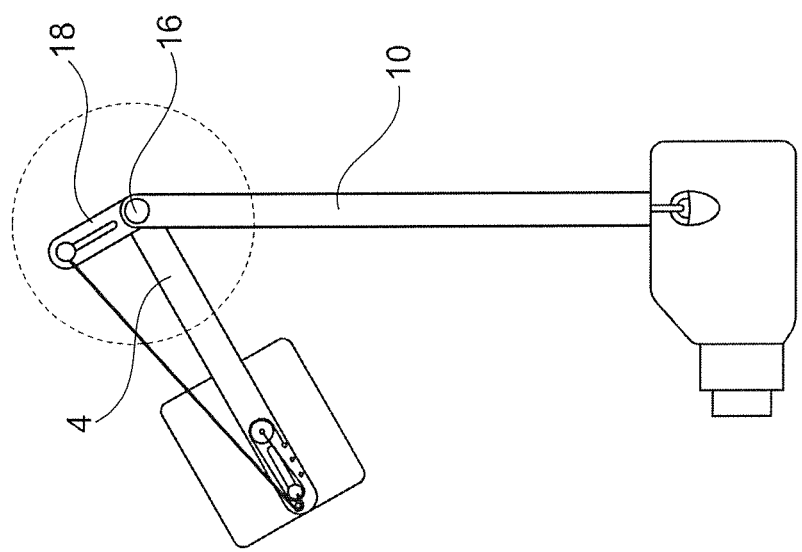

FIG. 5 depicts the configuration from FIG. 3 in the swiveled state. It is clear that an angle between the spacer element 4 of the arm support element 2 and the force support element 10 has been changed about the swivel axis 16. According to the invention, the angle is adjustable and as such it is possible to bring the force application lever 18, which is connected to the force transmission element 10 in the example of an embodiment shown, into the position depicted, in which it is also swiveled about the swivel axis 16 relative to the force transmission element 10. In this case, it is beneficial if the force application lever 18 can be brought into a first state and a second state, wherein it can be swiveled relative to the force application element 10 and relative to the spacer element 4 when in the first state.

Figure 6:
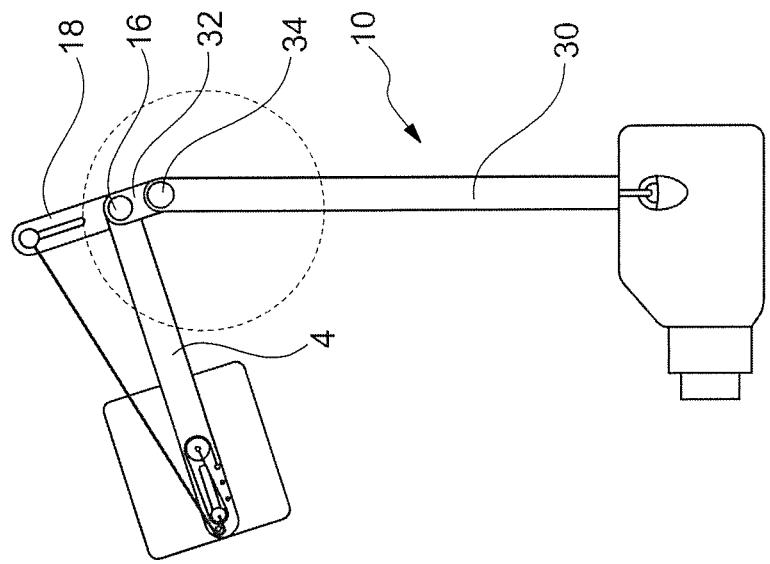

FIG. 6 shows an alternative configuration. The force transmission element 10 features a first structural component 30 and a second structural component 32, which are arranged adjacent to one another such that they can be swiveled about a swivel axis 34. Here, an angle between the first structural component 30 and the second structural component 32 can adjusted and set via the swivel joint 34, such that, once found, a position can be locked by way of the swivel joint 34. The spacer element 4 of the arm support element 2 is arranged such that it can be displaced about the swivel axis 16 relative to the second structural component 32.

Since the force application lever 18 is arranged relative to the second structural component 32 such that it is torque-proof, a swiveling of the second structural component 32 relative to the first component 30 about the swivel axis 34 also enables the adjustment of the angle between the force application lever 18 and the first structural component 30.

Figure 8:
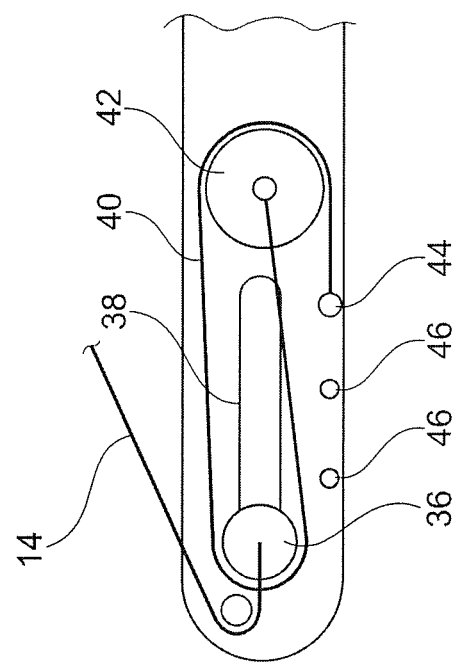
Figure 7:
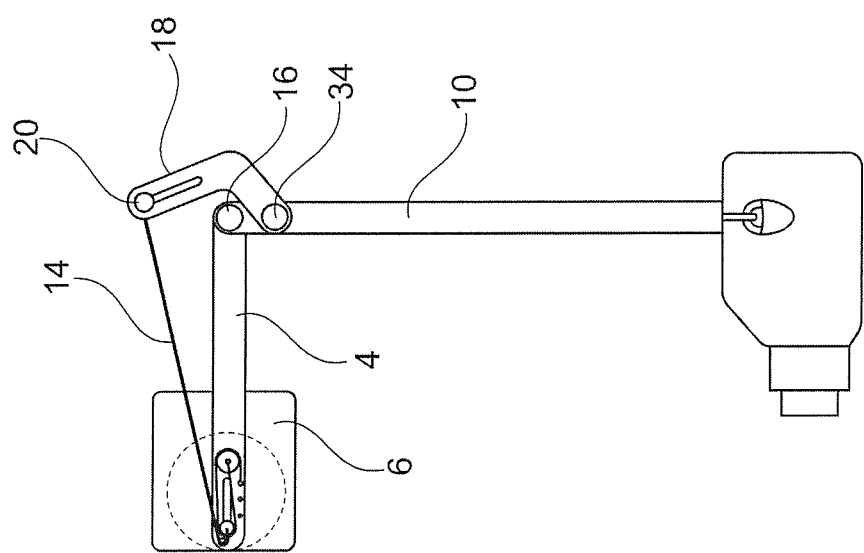

An alternative embodiment is shown in FIG. 7. In this case, the spacer element 4 of the arm support element 2 can again be swiveled relative to the force transmission element 10 about the swivel axis 16. The force application lever 18 is connected to the force transmission element 10 such that it is torque-proof but adjustable. A swivel joint 34 is provided for this purpose, thereby rendering the angle adjustable. The passive actuator 14 extends from a force application point 20 to an element in the region of the arm shell 6. FIG. 8 depicts an enlarged area. The passive actuator 14, arranged on a sliding roller 36, is clear to see. Said roller can be moved into an elongated hole 38, in which a cord element 40 is changed. A first end of the cord element 40 is arranged on a disc element 42, which forms part of the arm support element 2. The cord element 40 passes around the roller 36 and the disc element 42 and, in the example of an embodiment depicted, is fixed via a pin 44, which is inserted in a hole 46.

If the pin 44 is released from the state shown in FIG. 8 and inserted in one of the holes 46 arranged further to the left, this causes the roller 36 in the elongated hole 38 in the example of an embodiment shown to be displaced to the right. As a result, the passive actuator 14 is tensioned and the force acting on the force application lever 18 increased.

Figure 10:
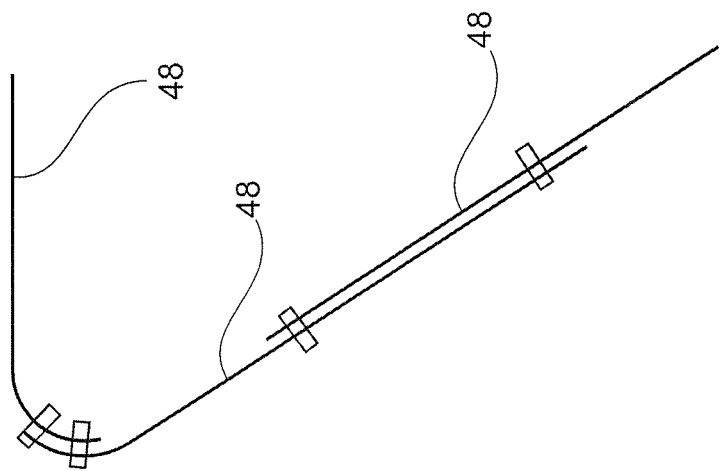
Figure 9:
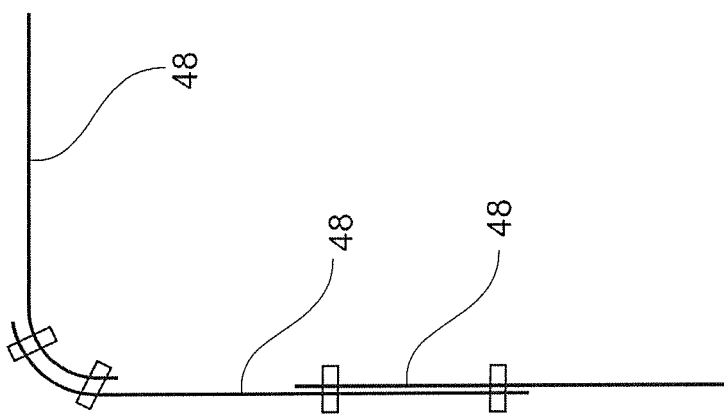

FIGS. 9 and 10 each depict a force transmission element 10, each of which consists of three partial elements 48. The three partial elements 48 are coupled in pairs, each by way of two connection elements, and exhibit the same radius of curvature in this area. They can thus be moved in relation to one another. As a result, the different radii of curvature between the two directions, in which the ends of the force transmission element extend, depicted in FIGS. 9 and 10 can be achieved. Specifically, the displacement of the two lower partial elements 48, which are designed to be straight in the section in which they are adjacent to one another, allows for the adjustment of the length of the force transmission element.

REFERENCE LIST 2 arm support element
4 spacer element
6 arm shell
8 counter bearing
10 force transmission element
12 counter bearing element
14 passive actuator
16 swivel axis
18 force application lever
20 force application point
22 lower end
24 pocket
26 tension element
28 swivel joint
30 first structural component
32 second structural component
34 swivel joint
36 roller
38 elongated hole
40 cord element
42 disc element
44 pin
46 hole
48 partial element

The invention claimed is:

1. A device for supporting at least one arm of a user, comprising:
   one or more arm support elements each of which has an arm shell for placing the at least one arm of the user on the arm shell,
   at least one passive actuator which is configured to apply a force to at least one of the one or more arm support elements,
   at least one counter bearing for the force to be applied by the at least one passive actuator, the at least one counter bearing comprising at least one force transmission element and a counter bearing element,
   at least one force application lever which is connected to at least one of the one or more arm support elements such that the connection between the at least one force application lever and the at least one of the one or more arm support elements permits (i) adjusting an angle between the at least one force application lever and the at least one of the one or more arm support elements and (ii) setting the angle between the at least one force application lever and the at least one of the one or more arm support elements so that the at least one force application lever is not rotatable relative to the at least one of the one or more arm support elements when the connection is torque-proof, and
   wherein the at least one passive actuator engages the at least one force application lever.

2. The device according to claim 1, wherein the at least one force application lever is positionable in a first state in which the at least one force application lever is swivellable relative to the at least one of the one or more arm support elements and the at least one force transmission element, and positionable in a second state in which the at least one force application lever is arranged with the at least one of the one or more arm support elements such that the connection between the at least one force application lever and the at least one of the one or more arm support elements is torque-proof.

3. The device according to claim 1, wherein the one or more arm support elements comprises two arm support elements.

4. The device according to claim 1 wherein the at least one passive actuator applies the force at a force application point that is displaceable.

5. The device according to claim 1 wherein the at least one force transmission element is arranged on the counter bearing element such that the at least one force transmission element is able to be rotated and/or swiveled.

6. A device for supporting at least one arm of a user, comprising:
   at least one arm support element which has an arm shell for placing the at least one arm of the user on the arm shell,
   at least one passive actuator which is configured to apply a force to the at least one arm support element,
   at least one counter bearing for the force to be applied by the at least one passive actuator, the at least one counter bearing comprising at least one force transmission element and a counter bearing element, and
   at least one force application lever switchable between a first state and a second state,
   wherein in the first state the at least one force application lever is rotatable relative to the at least one arm support element, and
   wherein in the second state the at least one force application lever is not rotatable relative to the at least one arm support element;
   wherein the at least one force application lever and the at least one arm support element are connected by a swivel joint; and
   wherein the swivel joint is tightenable to cause a switch from the first state to the second state and releasable to cause a switch from the second state to the first state.

7. The device of claim 6, wherein
   the first state permits adjusting an angle between the at least one force application lever and the at least one arm support element to any one of a plurality of positions, and
   the second state sets the angle to one locked position among the plurality of positions.

* * * * *